(12) United States Patent  
Mann

(10) Patent No.: US 6,468,988 B1
(45) Date of Patent: Oct. 22, 2002

(54) COMPOSITION THAT REGULATES AND DIMINISHES APPETITE AND METHODS RELATING THERETO

(76) Inventor: Morris A. Mann, 21669 N. 57th Ave., Glendale, AZ (US) 85308

( * ) Notice: Subject to any disclaimer, the term of this patent is extended or adjusted under 35 U.S.C. 154(b) by 0 days.

(21) Appl. No.: 09/515,586

(22) Filed: Feb. 29, 2000

Related U.S. Application Data

(60) Provisional application No. 60/122,308, filed on Mar. 1, 1999.

(51) Int. Cl.⁷ .......................... A61K 38/01; A61K 38/02; A61K 31/704; A61K 31/718; A61K 31/23
(52) U.S. Cl. ............................. 514/58; 514/2; 514/23; 514/783; 514/909; 514/552
(58) Field of Search ............................. 514/2, 23, 58, 514/783, 909, 552

(56) References Cited

U.S. PATENT DOCUMENTS 3,950,547 A * 4/1976 Lamar, III et al. ............ 426/74
6,171,640 B1 * 1/2001 Bringe ........................ 426/656

* cited by examiner

Primary Examiner—Edward J. Webman
Assistant Examiner—Helen Nguyen
(74) Attorney, Agent, or Firm—The Halvorson Law Firm

(57) ABSTRACT

A balanced composition of complex carbohydrate, protein, simple sugars, and lipids in the weight proportion of 3:2:1:1 substantially reduces appetite, even though the caloric composition is very low (about 240 cal per serving). This composition substantially facilitates weight loss, and increases exercise tolerance. It is designed for oral administration.

3 Claims, 1 Drawing Sheet

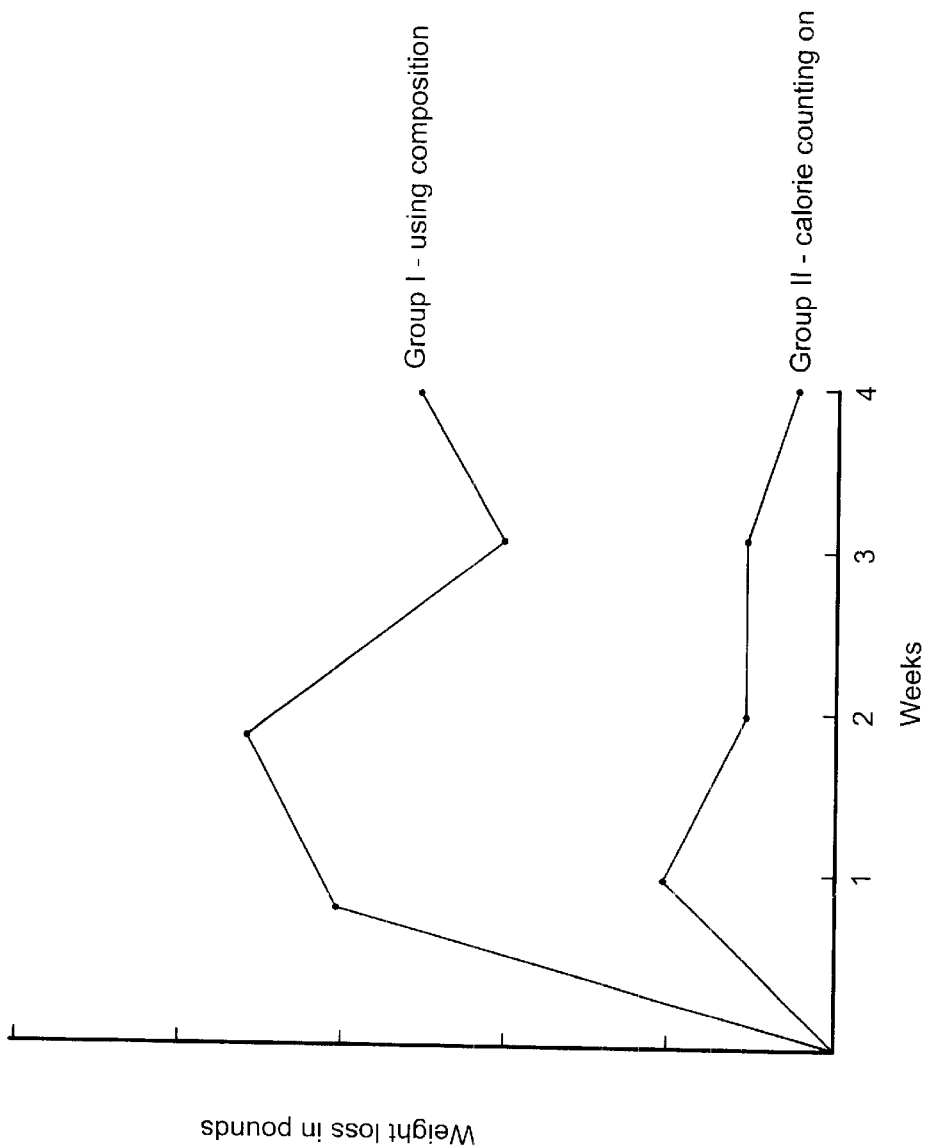

COMPOSITION THAT REGULATES AND DIMINISHES APPETITE AND METHODS RELATING THERETO

CROSS-REFERENCE TO RELATED APPLICATION

This application claims the benefit of U.S. Provisional Application No. 60/122,308, filed Mar. 1, 1999.

TECHNICAL FIELD

This invention relates generally to appetite suppression and, more specifically, to a composition of a complex carbohydrate, protein, simple sugar and lipid in a proportion of about 3:2:1:1, which increases satiation, thereby resulting in a reduction of food and caloric intake and leading to a decrease in weight.

BACKGROUND OF THE INVENTION

Obesity caused by excessively high caloric intake and accumulation of surplus fat often leads to various types of degenerative diseases. Dieting, bariatrics, and cytotherapy are of major concern to patients who suffer from obesity-caused diseases, as well as to healthy people who, for cosmetic reasons, wish to control their caloric intake and thereby modify their appearance. Dieting often requires that significant limitations be placed on caloric intake, and the amount of fat and carbohydrates consumed are invariably diminished in a successful dietary plan. However, most diets invariably fail because of a lack of satiation on the part of the dieting individual who is accustomed to a higher caloric intake.

Accordingly, there is a need in the art for a low calorie composition capable of inducing satiation for a substantial period of time. This invention fulfills these needs and provides other related advantages.

SUMMARY OF THE INVENTION

Briefly stated, in one embodiment, the present invention discloses a composition containing a complex carbohydrate, protein, simple sugar and lipid in relative weight proportion of about 3:2:1:1. The complex carbohydrate can include a variety of high molecular weight maltodextrins, dextrins, and the like. The protein contains all of the essential amino acids in an appropriate physiological balance. The simple sugar can contain fructose, glucose, sucrose, maltose, and the like, but is limited to a monosaccharide or disaccharide. The lipid is of an appropriate medium chain triglyceride and an oil in a ratio of 1:1. The oil may be mono-unsaturated, unsaturated, or saturated. Other optional components included vitamins, minerals, and long chain inulin.

In another embodiment, the present invention provides a method for increasing satiation with oral administration of an effective amount of a composition of this invention. In yet another embodiment, a method for manufacturing the present invention is disclosed.

BRIEF DESCRIPTION OF THE DRAWINGS

FIG. 1 is a graph illustrating weight loss in individuals administered a representative composition of this invention.

DETAILED DESCRIPTION OF THE INVENTION

The appetite satiation composition of the present invention contains a complex carbohydrate. A variety of different complex carbohydrates are suitable, including but are not limited to, dextrins, maltodextrins, and the like. A non-absorbable complex carbohydrate, inulin as a long chain preparation, is also found beneficial not only for its inherent ability to regulate blood sugar, but also for its value as a non-absorbable fiber.

Protein is also important in the composition of this invention. Suitable protein may be derived from animal or vegetable sources. Further, all of the essential amino acids should be present in appropriate physiological concentrations. Therefore, if soy protein is utilized, one must consider methionine supplementation, while the same concern is not necessary for dairy or animal protein preparations.

Simple sugars as utilized in the present invention are monosaccharides or disaccharides, although sugar alcohols, such as sorbitol, may also be used. Fructose, glucose, maltose., and sucrose are among the sugars that may be employed. The preferred simple sugar is fructose because it does not induce an excessive release of insulin, thereby contributing to rebound hypoglycemia and hunger.

Lipids of the present invention should derive at least half of their calories from a medium chain triglyceride, with caprylic/caproic acid being preferred. Other lipids include, but are not limited to, mono-unsaturated oils, such as olive oil, avocado oil and canola oil. Other oils that may be employed include soy oil, peanut oil, and the like.

To maintain the composition of this invention sufficient in terms of nutritional value, it is preferred that the composition be supplemented with vitamins and minerals so as to have at least one-third or up to the minimum daily requirement of the essential vitamins and minerals.

The examples that follow are provided for purposes of illustration, and are not intended to be limiting. The composition may be mixed in large quantities, using either a ribbon blender or a V-tower blender. Other mixing devices may be used, such as a Hobart blender or other similar equipment that achieves a uniform blend.

Ten individuals with obesity of long duration were given the composition as disclosed in Table 1 for 1 month. They were weighed weekly and pounds lost per week were then added up and divided by 10. Obesity is defined as weighing 30% more than one's expected ideal body weight. Long duration of obesity is defined as more than 5 years. Another group of 10 individuals was simply told to limit their caloric intake to under 1,600 calories/day for 1 month. As in the previous group, the amount of total weight lost I week was added and divided by 10. The results are depicted in FIG. 1. The individuals receiving the composition were advised to have 2 servings daily—one in the morning and one at noon. They were allowed to have dinner as they so desired. Clearly the group using the composition lost more weight, and the average time before hunger was felt after administration of the composition was 5 hours.

TABLE 1

| wt. % | Ingredient |
| --- | --- |
| 46.857 | Maltodextrin M180 |
| 22.0086 | Supro 675 |
| 12.7792 | Supro 670 |
| 10.9333 | Fructose |
| 1.41991 | MCT oil |
| 1.41991 | Bromelain 80 GDU |
| 1.32336 | PSND precore |
| 0.85195 | Inulin |
| 0.70995 | Guar Gum |

TABLE 1-continued

| wt. % | Ingredient |
|---|---|
| 0.70995 | Soybean Oil |
| 0.42597 | Sodium Carboxy Metha Cellulose 65% active |
| 0.21299 | Gum Carageenan 601 |
| 0.1495 | Aspartame (Nutrasweet) |
| 0.1495 | Vanilla CE25096 |
| 0.14199 | L-Methionine |
| 0.1361 | Anasthetic CE 26779 (vanilla) |

EXAMPLE 2

In a second experiment, 5 highly trained athletes were given the composition which consisted of the formula disclosed in Table 2. The total caloric content was 240 kcal. The individuals were then placed on an exercise ergometer (stationary bike) set at 300 watts. They were asked to peddle to exhaustion. One week later the same athletes indulged in the same experiment but were not given the composition. The difference in time spent when averaged was substantial, with the average difference between the two groups was 1 hour and 8 minutes. This is significant since the ergometer said they were consuming 964 calories/hour and the number of calories in the composition was only 240.

TABLE 2

| wt % | Ingredient: |
|---|---|
| 12.3208345 | Supro 670 |
| 21.219215 | Supro 675 |
| 45.1763933 | Maltodextrin M180 |
| 10.5411584 | Fructose |
| 0.20534724 | Gum Carageenan 601 |
| 0.41069448 | Cellulose Gum |
| 8 | Cocoa Powder (D11 SS) |
| 0.5 | Chocolate CE 23692 |
| 0.68449081 | Guar Gum |
| 0.01368982 | Vanilla CE 25096 |
| 0.12 | Anasthetic CE 26779 |
| 1.27589086 | PSND precore |
| 0.13689816 | L-Methionine |
| 0.28 | Aspartame Nutrasweet |
| 1.36898161 | MCT oil |
| 1.36898161 | Bromelain 80 GDU |
| 0.82138897 | Inulin |
| 0.68449081 | Soybean oil |

TABLE 2-continued

| Vitamins and Minerals PSND Precor (Powder Mix) | |
|---|---|
| Ea dose | Ingredient: |
| 330 | Calcium carbonate USP pwd |
| 132 | Magnesium carbonate USDP pwd |
| 19.8 | Vit. C |
| 19.8 | Vit. E acetate 50% D-L |
| 6.6 | Niacin |
| 5.94 | Iron peptonate |
| 4.95 | Zinc sulfate |
| 3.3 | Vit. A |
| 3.3 | D Calcium Pantothenoate pwd |
| 1.32 | Vit. D-3 100SD |
| 0.66 | Vit. B-6 |
| 0.66 | Copper |
| 0.66 | Manganese Carbonate |
| 0.56 | Vit. B-2 Riboflavin |
| 0.49 | Vit. B-1 HCl |
| 0.132 | Folic acid |
| 0.1 | Biotin USP Pure |
| 0.049 | Potassium iodine USP |
| 0.026 | Vit. K-1 |
| 0.023 | Sodium Selenite USP |
| 0.002 | Vit. B-12 |

From the foregoing it will be appreciated that, although specific embodiments of the invention have been described herein for purposes of illustration, various modifications may be made without deviating from the spirit and scope of the invention.

What is claimed is:

1. An appetite suppression composition comprising an effective amount of complex carbohydrate, protein, simple sugar and Lipid, wherein the weight ratio of the same is about 3:2:1:1 or 44%:28%:14%:14% by weight of the four components relative to each other.

2. A method for reducing caloric intake in a warm-blooded animal in need thereof, comprising orally administering to the animal a composition of claim 1.

3. A method for inducing a satiation in a warm-blooded animal in need thereof, comprising orally administering to the animal a composition of claim 1.

* * * * *